US012075198B2

(12) United States Patent
Takada et al.

(10) Patent No.: US 12,075,198 B2
(45) Date of Patent: Aug. 27, 2024

(54) IMAGE PROJECTION APPARATUS

(71) Applicant: PANASONIC CORPORATION, Osaka (JP)

(72) Inventors: Masahiro Takada, Kyoto (JP); Etsuro Hatano, Kyoto (JP); Takashi Nitta, Kyoto (JP); Satoru Seo, Kyoto (JP); Takashi Suzuki, Osaka (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 1001 days.

(21) Appl. No.: 17/060,469

(22) Filed: Oct. 1, 2020

(65) Prior Publication Data

US 2021/0021793 A1   Jan. 21, 2021

Related U.S. Application Data

(63) Continuation of application No. PCT/JP2019/012131, filed on Mar. 22, 2019.

(30) Foreign Application Priority Data

Apr. 4, 2018   (JP) ................. 2018-072647

(51) Int. Cl.
*H04N 9/31* (2006.01)
*A61B 5/00* (2006.01)
*A61B 90/00* (2016.01)

(52) U.S. Cl.
CPC ......... *H04N 9/3182* (2013.01); *A61B 5/0071* (2013.01); *A61B 90/36* (2016.02);
(Continued)

(58) Field of Classification Search
CPC .. H04N 9/3182; H04N 9/3185; H04N 9/3194; A61B 2090/366;
(Continued)

(56) References Cited

U.S. PATENT DOCUMENTS

| 5,772,593 A | 6/1998 | Hakamata |
| 2008/0004533 A1 | 1/2008 | Jansen et al. |

(Continued)

FOREIGN PATENT DOCUMENTS

| JP | H09-024053 A | 1/1997 |
| WO | 2005122906 A1 | 12/2005 |

(Continued)

OTHER PUBLICATIONS

International Search Report issued in corresponding International Application No. PCT/JP2019/012131, dated Jun. 11, 2019, with English translation.

(Continued)

*Primary Examiner* — Magda Cruz
(74) *Attorney, Agent, or Firm* — Rimon P.C.

(57) ABSTRACT

An image projection apparatus includes a detector that detects a first region emitting non-visible light; a projector that projects a visible-light image onto a second region including the first region detected by the detector; and a controller configured to generate the visible-light image. The controller varies colors of pixels of the visible-light image in a stepwise manner depending on emission intensities of the non-visible light at positions corresponding to the pixels within the first region.

6 Claims, 11 Drawing Sheets

(52) U.S. Cl.
CPC . *A61B 2090/366* (2016.02); *A61B 2090/3933* (2016.02); *A61B 2090/397* (2016.02)

(58) Field of Classification Search
CPC ...... A61B 2090/3933; A61B 2090/397; A61B 5/0537; A61B 5/414; G03B 21/12; G03B 29/00; G03B 42/06
See application file for complete search history.

(56) References Cited

U.S. PATENT DOCUMENTS

| | | |
|---|---|---|
| 2008/0051659 A1 | 2/2008 | Waki et al. |
| 2011/0160588 A1 | 6/2011 | Ichikawa |
| 2015/0230715 A1 | 8/2015 | Nahm et al. |
| 2017/0079741 A1 | 3/2017 | Makinouchi |
| 2017/0086940 A1* | 3/2017 | Nakamura ............. A61B 90/36 |
| 2017/0094236 A1* | 3/2017 | Kiriyama ............. H04N 9/3194 |
| 2017/0236022 A1 | 8/2017 | Abbas et al. |
| 2017/0272713 A1* | 9/2017 | Ehlert .................... H04N 23/11 |
| 2018/0014901 A1* | 1/2018 | Saito ....................... A61B 90/36 |
| 2018/0288404 A1* | 10/2018 | Ikehara ................ H04N 13/341 |
| 2019/0216573 A1* | 7/2019 | Nakamura ........... A61B 1/0005 |
| 2020/0152105 A1* | 5/2020 | Ishii ................... G02B 27/0172 |

FOREIGN PATENT DOCUMENTS

| | | |
|---|---|---|
| WO | 2010029888 A1 | 3/2010 |
| WO | 2016157260 A1 | 10/2016 |

OTHER PUBLICATIONS

International Preliminary Report on Patentability issued in International Patent Application No. PCT/JP2019/012131, dated Oct. 15, 2020.
Digital Trends: "Title: Flir One Thermal Imager for iOS and Andriod," Dec. 18, 2015 (Dec. 18, 2015), pp. 1-1, XP055796322, Retrieved from the Internet: URL:https://www.youtube.com/watch?v=quYGUAMaym8.
Mobile Tech Podcast: "Title: Flir One Pro Review Date of Publication," Jul. 7, 2017 (Jul. 7, 2017), pp. 1-1, XP055796331, Retrieved from the Internet: URL:https://www.youtube.com/watch?v=wY8s1hCNSMO.
Extended European Search Report issued in European Patent Application No. 19781597.0, dated Apr. 26, 2021.
Reconsideration Report by Examiner before Appeal dated Sep. 12, 2022 issued in the corresponding Japanese Patent Application No. 2018-072647, with English translation.
Communication Pursuant to Article 94(3) EPC dated Jan. 25, 2022 issued in the corresponding European Patent Application No. 19781597.0.
Notice of Reasons for Refusal issued on Feb. 22, 2022 in corresponding Japanese Patent Application No. 2018-072647; with English translation. .
Notice of Reasons for Refusal issued on Sep. 21, 2021 in corresponding Japanese Patent Application No. 2018-072647; with English translation.
Trial and Appeal Decision dated Mar. 14, 2023 issued in Japanese Patent Application No. 2018-072647, with English machine translation.
Notice of Reasons for Refusal dated Mar. 14, 2023 issued in Japanese Patent Application No. 2022-084021, with English machine translation.

* cited by examiner

Fig.4

| MODE | DISPLAY METHOD (DETAILS) | | ICG FLUORESCENCE EMISSION INTENSITY WEAK ⟶ STRONG ||||||||
|---|---|---|---|---|---|---|---|---|---|---|
| DISPLAY MODE | IR DISPLAY (FULL GRADATION) (HUE(H):--, SATURATION(S):FIXED AT S0, VALUE(V):VARIABLE) | | V0 (BLACK) ⟶ |||||| V100 (WHITE) ||
| FIRST PROJECTION MODE | COLOR CONVERSION (FULL GRADATION) (HUE(H):SELECTIVELY FIXED, SATURATION(S): VARIABLE, VALUE(V):FIXED AT V100) | | H240 S0 (WHITE) ⟶ |||||| H240 S100 (BLUE) ||
| SECOND PROJECTION MODE | MULTI-VALUED (MONOCOLORED) (HUE(H):SELECTIVELY FIXED, SATURATION(S): STEP, VALUE(V):FIXED AT V100) | 2-VALUED | H240 S0 (WHITE) |||| H240 S100 (BLUE) ||||
| | | 4-VALUED | H240 S0 (WHITE) || H240 S33 || H240 S67 || H240 S100 (BLUE) ||
| | | 8-VALUED | H240 S0 (WHITE) | H240 S14 | H240 S29 | H240 S43 | H240 S57 | H240 S71 | H240 S86 | H240 S100 (BLUE) |
| THIRD PROJECTION MODE | MULTI-VALUED (MULTICOLORED) (HUE(H):STEP, SATURATION(S): STEP, VALUE(V):VARIABLE) | | --- S0 V100 (WHITE) | H0 S20 V100 (RED) | H30 S40 V80 (ORANGE) || H60 S60 V80 (YELLOW) | H120 S80 V100 (GREEN) | H240 S100 V100 (BLUE) ||

Fig.10

| MODE | DISPLAY METHOD (DETAILS) | | ICG FLUORESCENCE EMISSION INTENSITY | | | | | | | |
|------|--------------------------|--|---|---|---|---|---|---|---|---|
| | | | WEAK →→→ STRONG | | | | | | | |
| DISPLAY MODE | IR DISPLAY (FULL GRADATION) (HUE(H):–, SATURATION(S):FIXED AT S0, VALUE(V):VARIABLE) | | V100 (WHITE) →→→ | | | | V0 (BLACK) | | | |
| FIRST PROJECTION MODE (INVERTED) | COLOR CONVERSION (FULL GRADATION) (HUE(H):SELECTIVELY FIXED, SATURATION(S): FIXED AT S100, VALUE(V):VARIABLE) | | H240 V0 (BLACK) →→→ | | | | H240 V100 (BLUE) | | | |
| SECOND PROJECTION MODE (INVERTED) | MULTI-VALUED (MONOCOLORED) (HUE(H):SELECTIVELY FIXED, SATURATION(S): FIXED AT S100, VALUE(V):STEP) | 2-VALUED | H240 V0 (BLACK) | | | | H240 V100 (BLUE) | | | |
| | | 4-VALUED | H240 V0 (BLACK) | | H240 V33 | | H240 V67 | | H240 V100 (BLUE) | |
| | | 8-VALUED | H240 V0 (BLACK) | H240 V14 | H240 V29 | H240 V43 | H240 V57 | H240 V71 | H240 V86 | H240 V100 (BLUE) |
| THIRD PROJECTION MODE (INVERTED) | MULTI-VALUED (MULTICOLORED) (HUE(H):STEP, SATURATION(S): VARIABLE, VALUE(V):STEP) | | — S100 V0 (BLACK) | H0 S100 V20 (RED) | H30 S80 V40 (ORANGE) | | H60 S80 V60 (YELLOW) | H120 S100 V80 (GREEN) | H240 S100 V100 (BLUE) | |

IMAGE PROJECTION APPARATUS

CROSS REFERENCE TO RELATED APPLICATIONS

The present application is a continuation of PCT/JP2019/012131 filed Mar. 22, 2019, which claims priority to Japanese Patent Application No. 2018-072647, filed Apr. 4, 2018, the entire contents of each of which are incorporated herein by reference.

BACKGROUND

1. Technical Field

The present disclosure relates to an image projection apparatus projecting a visible-light image onto a region from which non-visible light emission has been detected.

2. Related Art

JP 9-24053 A (Document 1) discloses a surgical operation support system allowing a fluorescent imager to output image data indicative of an affected area of a living body subjected to a surgical operation and reproducing an image based on the above image data by an image projector, for display on the actual affected area. A substance emitting fluorescent light by irradiation of light of a predetermined wavelength is applied in advance to the living body affected area. That is, this system supports confirmation of lesions by displaying a fluorescence image fluoresced from the affected area onto the actual affected area.

WO2016/157260 (Document 2) discloses a visible-light projection device including a detector detecting a first region emitting non-visible light, a projector performing projection using visible light, onto a second region including the first region detected by the detector, and a controller causing the projector to perform projection, based on color selected by the operator. If first color is selected as color of visible light projected by the projector onto a region of the second region other than the first region, the controller informs the operator that color of visible light projected by the projector onto the first region can be selected from among first options. On the other hand, if second color different from the first color is selected as color of visible light projected by the projector onto a region of the second region other than the first region, the controller informs the operator that color of visible light projected by the projector onto the first region can be selected from among second options different from a candidate combination included in the first options. Document 2 further discloses that in the case of allowing the projector to perform projection colored in multi-gradations onto the first region depending on the intensity of non-visible light from portions making up the first region detected by the detector, the saturation of color of visible light projected by the projector is set differently depending on the gradations. Such a configuration enables a video projection with a high visibility to be implemented.

SUMMARY

The present disclosure provides an image projection apparatus capable of implementing a video projection with a high visibility.

An image projection apparatus according to the present disclosure includes: a detector that detects a first region emitting non-visible light; a projector that projects a visible-light image onto a second region including the first region detected by the detector; and a controller configured to generate the visible-light image. The controller varies colors of pixels of the visible-light image in a stepwise manner depending on emission intensities of the non-visible light at positions corresponding to the pixels within the first region.

According to the present disclosure, an image projection apparatus capable of projecting a high-visibility image can be provided.

BRIEF DESCRIPTION OF DRAWINGS

FIG. 4 is a view explaining the contents of color conversion processing in a display mode and projection modes by the surgery support system.

FIG. 10 is a view explaining the contents of color conversion processing in a black-and-white inverted version in the display mode and the projection modes by the surgery support system.

DETAILED DESCRIPTION OF EMBODIMENTS

Embodiments of an image projection apparatus of the present disclosure will now be described in detail with appropriate reference to the drawings. Note, however, that unnecessarily detailed explanations may be omitted. For example, detailed explanations of already well-known matters or duplicate explanations for substantially the same configurations may be omitted. This is for the purpose of avoiding unnecessarily redundancy in the following description to facilitate the understanding of those skilled in the art.

It is to be noted that the applicant provides the accompanying drawings and the following description in order for those skilled in the art to fully understand the present disclosure but do not intend to thereby limit subject matters described in claims. Hereinafter, an example will be described where a projection system of the present disclosure is applied to a surgery support system used in hospitals.

First Embodiment

1. Overview of Surgery Support System

Figure 1:
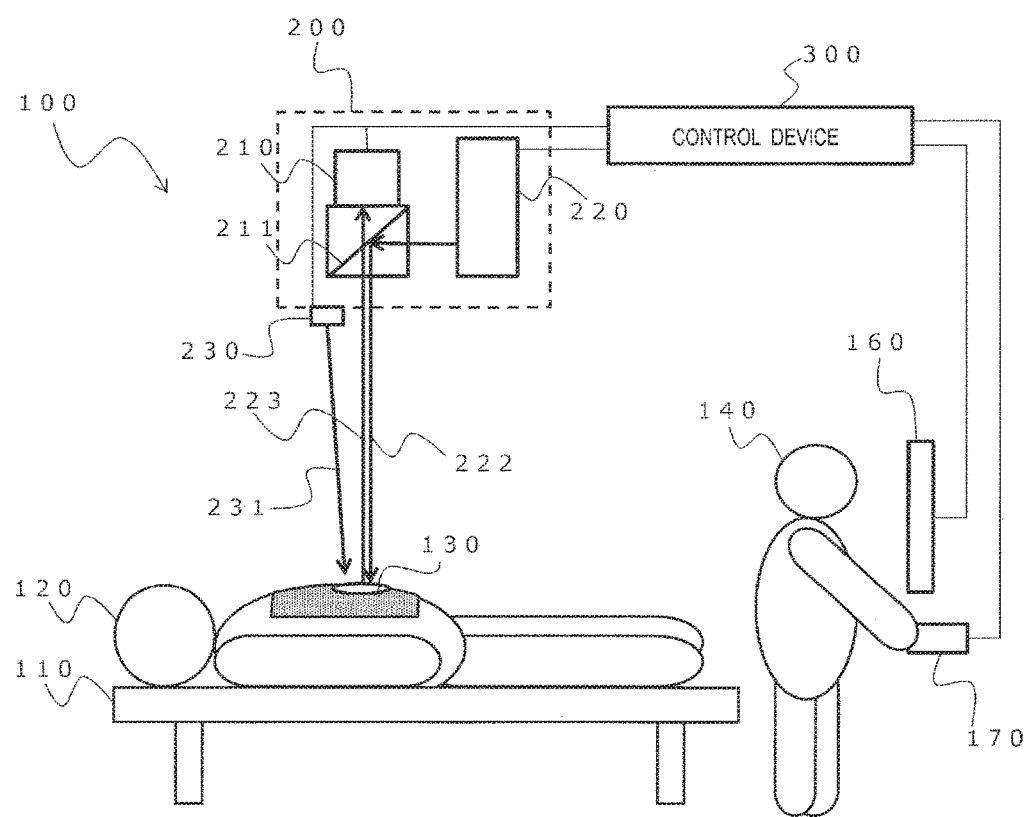
FIG. 1 is a view explaining a configuration of a surgery support system of an embodiment of the present disclosure.

FIG. 1 is a view explaining a configuration of a surgery support system that is an embodiment of an image projection system of the present disclosure. As shown in FIG. 1, a surgery support system 100 is disposed vertically above a patient 120 lying on a surgical table 110 and includes an image projection apparatus 200 that projects an image onto an affected area of the patient.

Before surgery utilizing the surgery support system 100, a photosensitive substance is administered in blood, etc. of the patient 120 undergoing surgery. The photosensitive substance is a substance that receives excitation light and emits fluorescent light. In this embodiment, indocyanine green (hereinafter, referred to as "ICG") is used as an example of the photosensitive substance. ICG is a medically approved reagent that can be used on the human body. When administered into blood, ICG accumulates on the affected area 130 where blood or lymph flow is disrupted. When irradiated with infrared excitation light around 800 nm, ICG emits infrared fluorescent light of a wavelength around 850 nm of peak wavelength. Accordingly, if a region (hereinafter, referred to as "ICG light-emitting region") emitting infrared fluorescent light can be detected, it becomes possible to identify a region of the affected area 130.

The surgery support system 100 detects the ICG light-emitting region to identify the region of the affected area 130. To allow the identified region of the affected area 130 to be visible to the doctor, the surgery support system 100 projects a visible-light image generated correspondingly to the identified region of the affected area 130, as a projection image, onto a region including the ICG light-emitting region, in a superimposed manner. In particular, the visible-light image includes an image having a region corresponding to the ICG light-emitting region colored with a high visibility color. By this projected visible-light image, the surgery support system 100 can support doctor's region identification (visual recognition) of the affected area 130 when performing surgery on the affected area 130.

In particular, the surgery support system 100 of this embodiment can project with the visible-light image (projected image) region colors differing depending on the emission intensity of the ICG light-emitting region. That is, ICG emission intensity distribution (ICG concentration distribution) can be projected in multiple colors, enabling the doctor, etc. to visually easily recognize the ICG concentration distribution. By allowing the ICG concentration distribution to be visually recognized in this manner, it becomes possible to easily confirm the range of the affected area 130 and the depth of a location where the affected area 130 is present in organ, 2. Configuration of Surgery Support System Configuration details of the surgery support system 100 will be described. The surgery support system 100 is disposed and used in an operating room of a hospital. As shown in FIG. 1, the surgery support system 100 includes the image projection apparatus 200, a control device 300, and an infrared excitation light source 230. The surgery support system 100 includes a display 160 and an operating part 170, for accepting various setting operations from an operator 140.

Although not shown, the surgery support system 100 includes a mechanism (a driving arm mechanically connected to the image projection apparatus 200, casters of a pedestal on which a set of the surgery support system 100 is mounted, etc.) for changing a position to dispose the image projection apparatus 200.

The image projection apparatus 200 is an apparatus that integrally encompasses imaging means and irradiation means. The image projection apparatus 200 includes an infrared camera 210, a dichroic mirror 211, and a projector 220. The image projection apparatus 200 detects infrared fluorescent light 223 issued from the patient 120 lying on the surgical table 110. The image projection apparatus 200 then irradiates visible irradiation light 222 from the projector 220 onto a region including the region (ICG light-emitting region) of the affected area 130 indicated by the detected infrared fluorescent light 223. In order to detect the infrared fluorescent light 223 more properly and to irradiate the visible irradiation light 222 more properly, it is preferred that the image projection apparatus 200 be disposed right above the patient 120 lying on the surgical table 110.

The control device 300 is a device that overall controls actions of parts making up the surgery support system 100. The control device 300 connects to and controls the infrared camera 210, the projector 220, and the infrared excitation light source 230.

Figure 2:
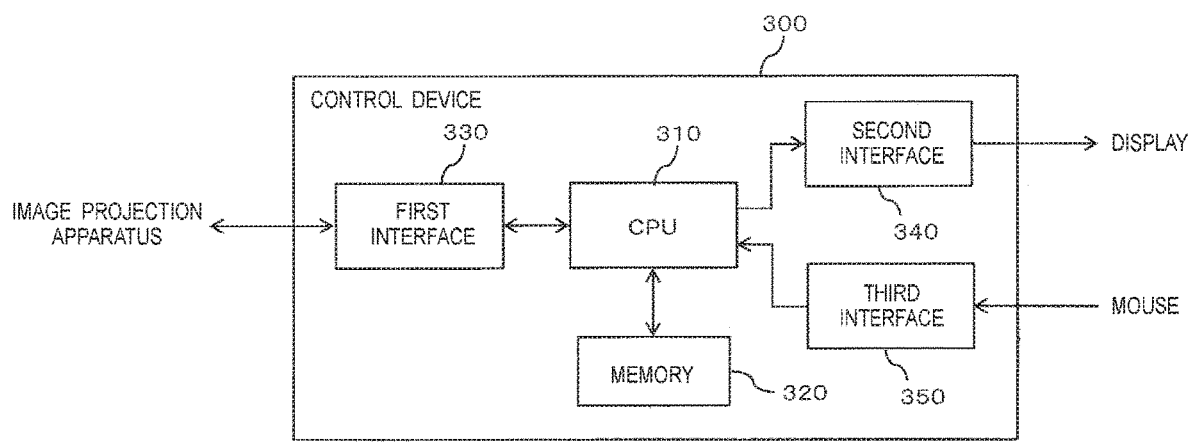
FIG. 2 is a block diagram showing a configuration of a control device of the surgery support system.

FIG. 2 is a block diagram showing an internal configuration of the control device 300. As shown in FIG. 2, the control device 300 includes a CPU 310 and runs a predetermined program to thereby implement predetermined functions. Instead of the CPU 310, another type of general-purpose processor, e.g. an MPU may be used. Alternatively, instead of the CPU 310, a processor dedicatedly designed so as to implement predetermined functions may be used. That is, the control device 300 can include various processors (semiconductor devices) such as CPU, MPU, FPGA, DSP, and ASIC.

Furthermore, the control device 300 includes a memory 320 and first to third interfaces 330 to 350. The memory 320 is a medium that stores information and programs required when the CPU 310 executes calculations, and is properly accessed from the CPU 310.

The first interface 330 is a communication circuit through which the control device 300 interchanges data and commands with the image projection apparatus 200, The control device 300 sends a control command to the infrared excitation light source 230 via the first interface 330. The control device 300 receives an infrared image via the first interface 330 from the infrared camera 210. The control device 300 sends a control signal via the first interface 300 to the projector 220.

The second interface 340 is a communication circuit through which the control device 300 sends a video signal to the display 160. The third interface 350 is a communication circuit through which the control device 300 receives an operation signal from the operating part 170. The first to the third interfaces 330 to 350 perform interchange of data and commands in accordance with a prescribed communication standard (e.g. USB standard, HDMI (registered trademark) standard).

Referring back to FIG. 1, the infrared excitation light source 230 is a light source that irradiates infrared excitation light 231 at least of the order of 800 nm that is an ICG excitation wavelength. The infrared excitation light source 230 includes a light-emitting element (e.g. LED) that emits infrared light around 800 nm. The infrared excitation light source 230 can switch irradiation ON/OFF of the infrared excitation light 231 in accordance with a control signal from the control device 300. In order to reduce irradiation unevenness of the infrared excitation light 231, it is preferred that the infrared excitation light source 230 be disposed right above the patient 120 lying on the surgical table 110.

The display 160 can display, for example, an image (hereinafter, referred to as "fluorescence image") of the detected ICG light-emitting region, and a menu for performing various settings in a projection action of the control device 300.

The operator 140 can perform various settings in the projection action of the control device 300 by operating the operating part 170 while looking at the menu and icons appearing on the display 160. For example, the projection mode of the projector 220 can be set. It is also possible to perform settings of color (hue) and number of gradations of light projected on the ICG light-emitting region (affected area 130). It is also possible to perform switch settings of color and number of gradations of light projected on the surroundings (background) and contours of the ICG light-emitting region. The control device 300 accepts a setting operation from the operator 140 to perform a projection action depending on the operation setting.

The display 160 can be configured from an LCD display, an organic EL display, etc. The operating part 170 is an input device, such as a keyboard, a mouse, a touch panel, and a stylus pen, with which the operator 140 performs instructions and settings.

Details of parts of the image projection apparatus 200 will hereinafter be described.

The infrared camera 210 is a camera having spectral sensitivity characteristics in the infrared region. The surgery support system 100 needs to detect the infrared fluorescent light 223 around 850 nm emitted from ICG of the patient 130. To that end, the infrared camera 210 has spectral sensitivity characteristics for the infrared region at least of the order of 850 nm. In order to avoid receiving light other than the infrared fluorescent light 223 emitted from ICG, a bandpass filter allowing only light of a wavelength around 850 nm to pass therethrough may be disposed in front of the infrared camera 210. The infrared camera 210 transmits an infrared image obtained by imaging to the control device 300.

The projector 220 is a projection device that projects a visible-light image in accordance with a control signal from the control device 300, The projector 220 may irradiate light of any wavelength (color) as long as it is light within the visible-light region visible by humans. The projector 220 is configured to irradiate light of a plurality of wavelengths (colors) switchable in accordance with a control signal from the control device 300. The projector 220 irradiates the visible irradiation light 222 toward the dichroic mirror 211.

The dichroic mirror 211 is disposed facing each of the infrared camera 210 and the projector 220. The dichroic mirror 211 is an optical element having a function of reflecting light of a specific wavelength but transmitting light of other wavelengths. In the present disclosure, a projection port of the projector 220 is arranged in the horizontal direction of the dichroic mirror 211, while the infrared camera 210 is arranged vertically above the dichroic mirror 211. The dichroic mirror 211 has an optical characteristic of reflecting visible irradiation light 222 irradiated from the projector 220 but transmitting infrared fluorescent light 223 heading toward an imaging surface of the infrared camera 210. As shown in FIG. 1, the visible irradiation light 222 reflected by the dichroic mirror 211 and the infrared fluorescent light 223 incident on the imaging surface of the infrared camera 210 have the same optical path. This can enhance the accuracy of irradiation of the visible irradiation light 222 onto the region (affected area 130) issuing the infrared fluorescent light 223.

In the above, the infrared camera 210 is an example of a detector of the present disclosure. The projector 220 is an example of a projector that performs projection using visible light of the present disclosure. The control device 300 is an example of a controller of the present disclosure. And, the surgery support system 100 is an example of the image projection apparatus of the present disclosure.

3. Actions of Surgery Support System

Figure 3:
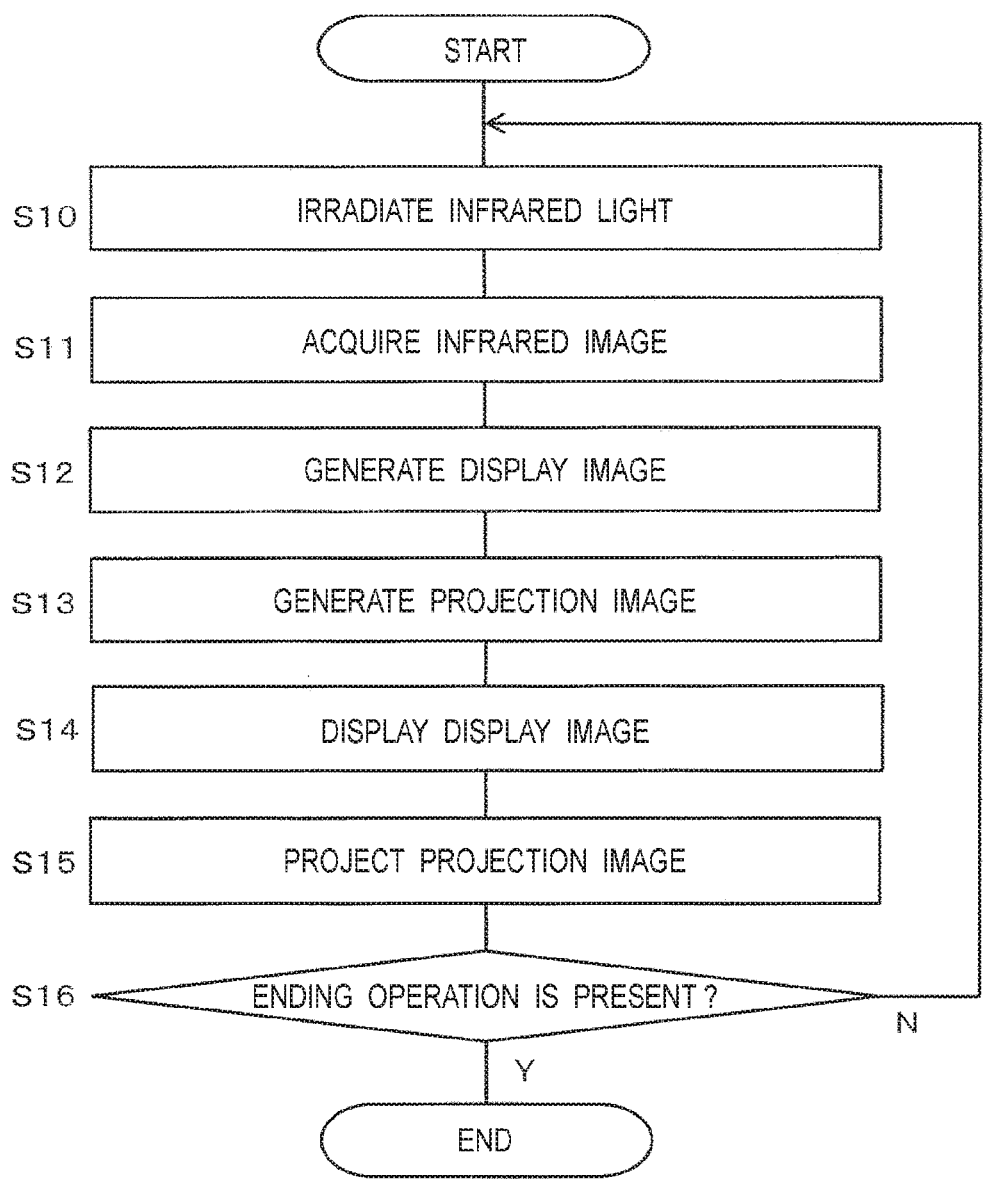
FIG. 3 is a flowchart showing actions of the surgery support syste.

FIG. 3 is a flowchart showing actions of the surgery support system 100. Referring to the flowchart of FIG. 3, actions of the surgery support system 100 will be described.

The infrared excitation light source 230 irradiates infrared light onto the affected area 130 of the patient 120 (Step 10). ICG accumulated in the affected area 130 emits infrared fluorescent light when receiving infrared light. The infrared camera 210 images a region including the affected area 130 to generate an infrared image.

Via the first interface 330, the control device 300 acquires the infrared image imaged and generated by the infrared camera 210 (Step 11). From the infrared image, the control device 300 (i.e. CPU 310) generates a display image for display on the display 160 (Step 12). That is, the control device 300 generates the display image, based on the emission intensity of the ICG light-emitting region in the acquired infrared image (i.e. the pixel signal strength of the infrared image) (Step 12).

Furthermore, from the infrared image, the control device 300 generates a projection image for projection onto the ICG light-emitting region (Step 13). Generation processes of the display image and the projection image will be described later.

And, the control device 300 sends the generated display image to the display 160, allowing display on the display 160 (Step 14). The control device 300 sends data of the generated projection image to the image projection apparatus 200, allowing the projector 220 to project the projection image with visible light (Step 15).

Until accepting an ending operation related to the projection actions of the surgery support system 100 (Step 16), the control device 300 executes the above processes (Step 10 to Step 15) repeatedly. This allows visible-light projection image to be projected onto the ICG light-emitting region of the affected area 130, enabling the doctor to visually easily recognize a medical treatment area, etc.

3.1 Color Control of Display Image and Projection Image

Description will be given of color control on the display image or the projection image by the surgery support system 100.

The surgery support system 100 has one display mode as an action mode of the display 160. The surgery support system 100 has first to third projection modes as projection modes of the projector 220. Although a display image or a projection image is generated from an infrared image in each mode, the color conversion processing manner at that time differs by mode.

FIG. 4 is a view explaining color control of the display image and the projection image in the display mode and the first to third projection modes in the surgery support system 100. In a table shown in FIG. 4, a first stage explains control on color of the display image in the display mode, while second to fourth stages explain control on color of the projection image in each projection mode.

Figure 5:
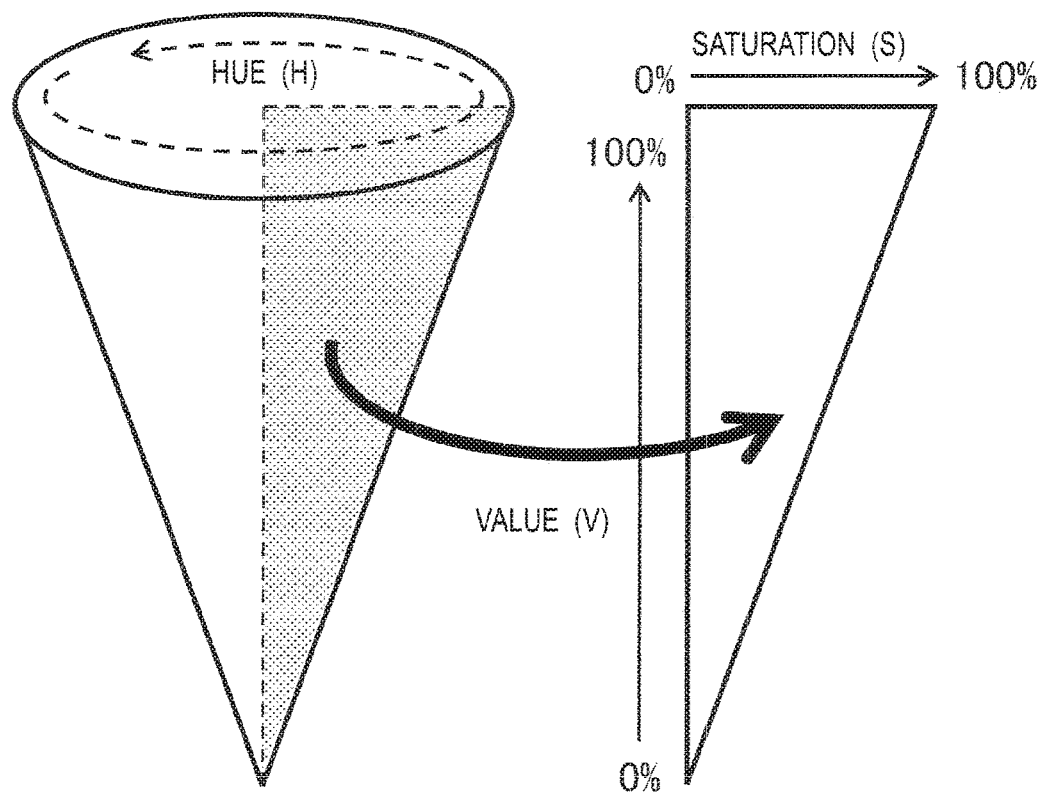
FIG. 5 is a view explaining an HSV color space.

FIG. 5 is a view explaining a general HSV color space. The HSV color space expresses colors by Hue (H), Saturation (S), and Value (V). Hue (H) represents a color type such as red, blue, and yellow, except white and black. Saturation (S) is color vividness and takes a value from 0 to 100%. Value (V) is color brightness and takes a value from 0 to 100%. White is when the saturation is 0% with the value being 100%, and black is when the saturation is 0% with the value being 0%.

In the following description, H0 means that the hue is 0 degree, H120 means that the hue is 120 degrees, S0 means that the saturation is 0%, S100 means that the saturation is 100%, V0 means that the value is 0%, and V100 means that the value is 100%, and the same applies to the other notations. The subsequent HSV numerical values are one example, and e.g. any numerical values other than H0 may be employed as long as the operator is recognizable as red. Furthermore, color may be set using a color space, such as RGB color segment, other than the HSV color space.

Hereinafter, referring to FIG. 4, color control in the display mode and the first to third projection modes will be described.

(1) Display Mode

A display image appearing on the display 160 is generated by color-converting an infrared image (esp. a fluorescence image including the ICG light-emitting region) received from the infrared camera 210. The display image is displayed in black and white. That is, the display image is generated by color-converting the color of each pixel of the infrared image as follows. Specifically, for each pixel of the infrared image, the saturation (S) is fixed at 0% (S0) (minimum) while the value (V) is set within a range from 0 to 100% (V0 to V100) depending on the brightness (fluorescence emission signal intensity) of each pixel of the infrared image. The value (V) of the display image is set to a higher value according as the infrared image has a stronger brightness. As to the hue, any value is acceptable since the saturation is 0%. The gradation of the display image is set to the maximum gradation (1024 gradations in this embodiment).

(2) Projection Mode

A projection image projected by the projector 220 is generated by color-converting an infrared image (esp. a fluorescence image) received from the infrared camera 210. Note that in the projection mode, the background other than the affected area in the infrared image is displayed in white so as to fulfill the function as lighting.

a) First Projection Mode

A first projection mode is a mode for generating a projection image by color-converting an infrared image in full gradation (1024 gradations). In the first projection mode, the hue of each pixel of the projection image is fixed at a hue (e.g. H240 in FIG. 4) selected by the operator and the value is fixed at 100%. The saturation (S) of each pixel of the projection image is set depending on the brightness, i.e. ICG fluorescence emission intensity, of the infrared image. In the example of FIG. 4, color (color visually recognized by the operator) of each pixel of the projection image turns from white into blue according as the ICG fluorescence emission intensity becomes stronger.

b) Second Projection Mode

A second projection mode is a mode in which the number of gradations in the first projection mode is reduced and is a mode displaying, in monocolor, a projection image obtained by mufti-valuing the infrared image. In the second projection mode, a monocolored projection image is generated by binarizing, quaternarizing, or octalizing the infrared image based on the pixel brightness. The gradation of the projection image is previously set in the control device 300 by the operator 140 via the operating part 170. Similar to the first projection mode, in the second projection mode, the hue (H) is fixed at a hue (e.g. H240 in FIG. 4) previously selected by the operator, the value (V) is fixed at 100%, and the saturation (S) is set depending on the brightness (ICG fluorescence emission intensity) of the infrared image.

For example, in the case of displaying a 2-valued image, the hue (H) and the value (V) are fixed and the saturation (S) is set to S0 or 3100 depending on the brightness of the infrared image. Or, in the case of displaying a 4-valued image, the saturation (3) is set to any one of S0, S33, S67, and 3100 depending on the brightness of the infrared image. By virtue of such a second projection mode, the visibility at the boundary of the projection image is improved.

c) Third Projection Mode

A third projection mode is a mode in which a projection image obtained by multi-valuing an infrared image is displayed in multicolor. In the third projection mode, a multicolored projection image is generated by multi-valuing the infrared image based on the pixel brightness. In the third projection mode, the hue (H) is set to any one of 6 types (–H0, H30, H60, H120, H240) depending on the brightness of the infrared image. The saturation (S) is set to any value of 6 steps (S0, S20, S40, S60, S80, S100) depending on the brightness of the infrared image. The value (V) is also varied depending on the brightness of the infrared image. In the third projection mode, an image is displayed using different colors that depend on the ICG fluorescence intensity, so that an image colored differently for each distribution of the ICG fluorescence intensity is projected onto the ICG light-emitting region of the affected area 130. This leads to an improved visibility of the ICG concentration distribution in the affected area 130.

Note that, since white appears irrespective of the value of the hue if the saturation is 0% and the value is 100%,—(any value) is given to a portion having the lowest ICG light emission intensity. Moreover, if the ICG fluorescence emission intensity is less than a predetermined value, white is given that is the same color as the background having the ICG fluorescence emission intensity of 0.

The color (color visually recognized by the operator) of each pixel of a projection image is displayed in 6 stages of white, red, orange, yellow, green, and blue according as the ICG fluorescence emission intensity increases.

Although the value may be constant, generally, orange and yellow have a lower visibility according as the value becomes higher, so that they are given a little lower value as compared with the other colors, to improve the visibility.

Figure 6:
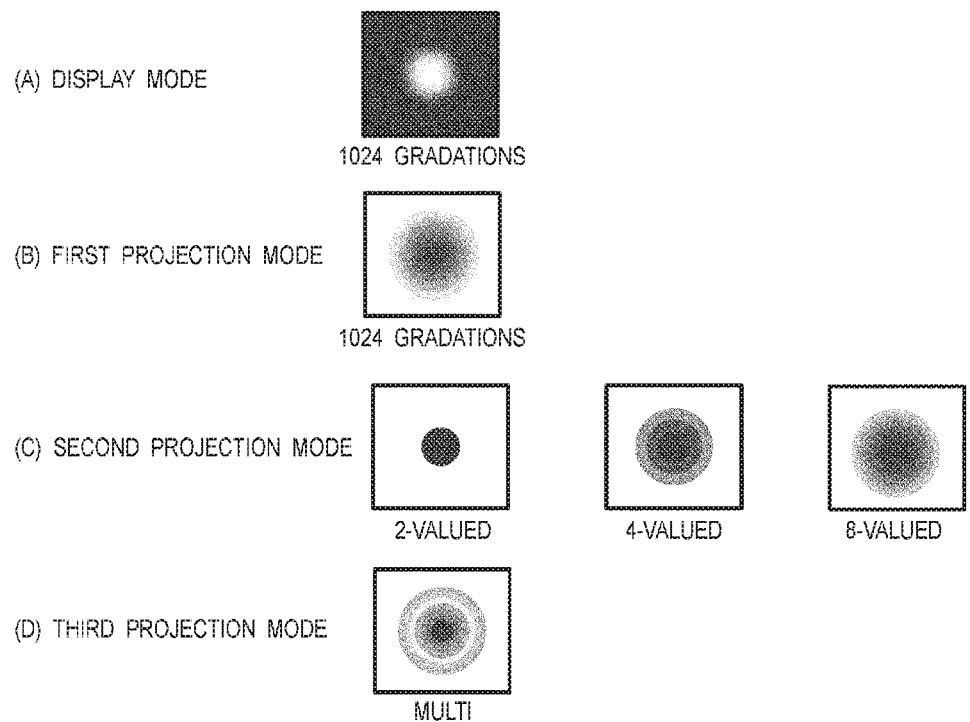
FIG. 6 is a view explaining images of an image displayed or projected in each of the display mode and the projection modes.

FIG. 6 is a view showing, in contrast, examples of an image displayed in the display mode and of images projected in the first to third projection modes. FIG. 6(A) shows an example of a black and white image in full gradations (1024 gradations), displayed on the display 160 in the display mode. FIG. 6(B) shows an example of a monocolored image in full gradation, projected from the projector 220 in the first projection mode. FIG. 6(C) shows examples of a monocolored multi-valued image, projected from the projector 220 in the second projection mode. FIG. 6(C) shows a 2-valued image, a 4-valued image, and an 8-valued image, individually. FIG. 6(D) shows an example of a multi-colored multi-valued image, projected from the projector 220 in the third projection mode.

Figure 7A:
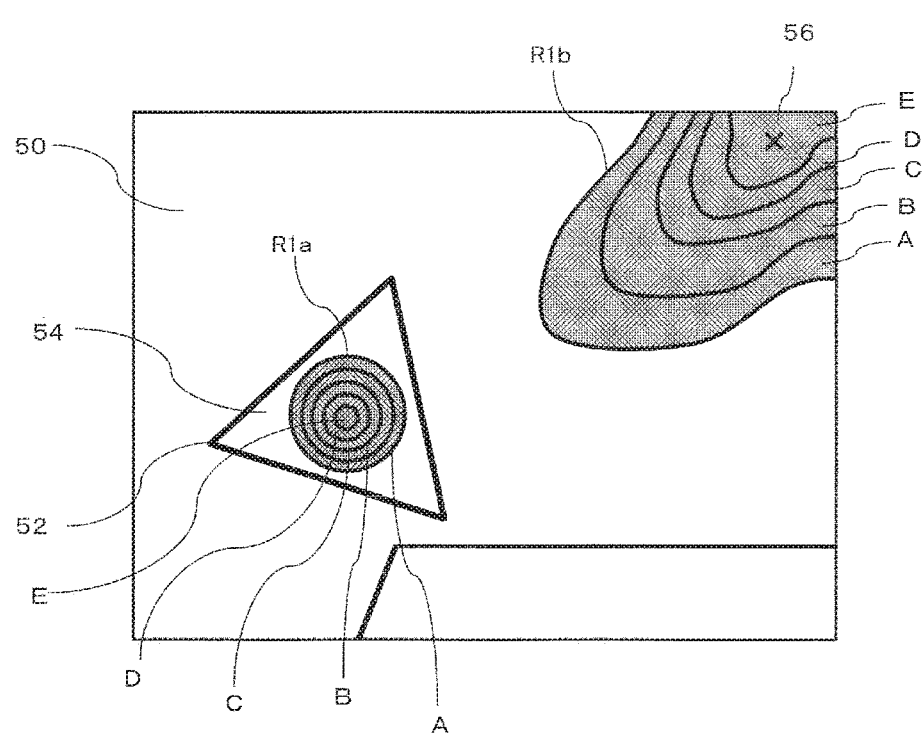
FIG. 7A is a view explaining an image of an infrared image imaged by an infrared camera.
Figure 7B:
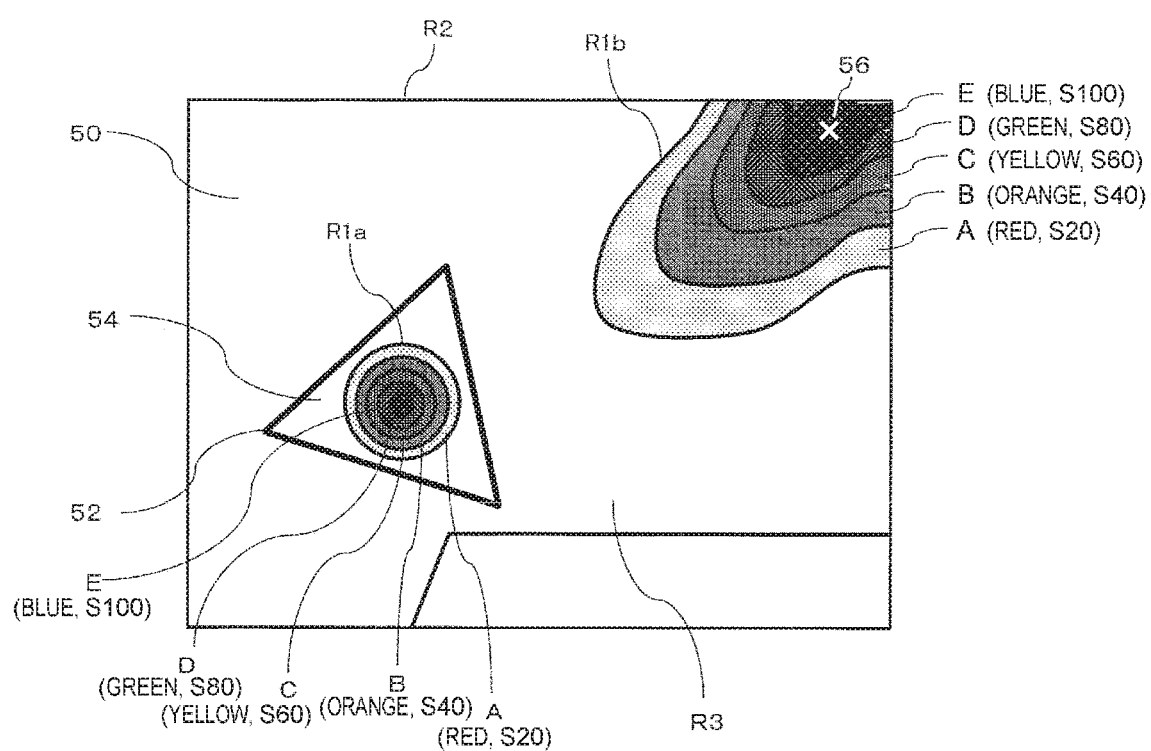
FIG. 7B is a view explaining an image of a projection image projected in a third projection mode (multi-colored projection mode), onto the infrared image shown in FIG. 7A.

FIG. 7A is a view explaining an image of an infrared image imaged by the infrared camera. In FIG. 7A, there is an incision 52 in a body surface 50 of the patient 120. ICG is accumulated in a region R1a in an interior 54 of the patient body, visible from the incision 52. A region Rib around an ICG injection part 56 is also an ICG accumulated portion. In affected areas A to E within these regions R1a and R1b, ICG is accumulated in respective different concentrations. In this case, the affected areas E to A have an ICG concentration lowered in the mentioned order. Thus, the affected area E has a strongest ECG fluorescence emission intensity, and the affected areas D, C, B, and A have an ICG fluorescence emission intensity weakened in the mentioned order. From the infrared image, the CPU 310 detects the regions Ria and Rib (an example of a first region) where fluorescence is seen, to color-convert pixels of these regions R1*a* and R1*b* in the infrared image to generate a projection image, FIG. 7B is a view showing an image of a projection image generated from the infrared image shown in FIG. 7A in the third projection mode. An overall region R2 (an example of a second region) of the projection image shown in FIG. 7B includes the detected regions R1*a* and R1*b* and a background region R3 thereof. In the projection image, pixels in the portion of the affected area E having a strongest ICG fluorescence emission intensity are set to blue in hue and to S100 in saturation. Pixels in the portion of the affected area D having a next strongest ICG fluorescence emission intensity are set to green in hue and to S80 in saturation. Pixels in the portion of the affected area C having a further next strongest ICG fluorescence emission intensity are set to yellow in hue and to S60 in saturation. Hereinafter, similarly, pixels in the portion of the affected area B are set to orange in hue and to S40 in saturation. Pixels in the portion of the affected area A are set to red in hue and to S20 in saturation. In this manner, respectively differently colored projection images are generated for the affected areas A to E. The background region R3 is white. As shown in 7B, images colored differently depending on the ICG fluorescence intensity distribution are projected, with the result that the intensity distribution is visually recognized more easily.

By allowing the ICG fluorescence intensity distribution to be visually recognized, it becomes possible to easily confirm the range of the affected area 130 or the depth of a site where the affected area 130 exists in an organ. For example, in the case where the affected area 130 is deeply buried in the organ, ICG fluorescence emission detected on the body surface 50 is weak, so that it is projected as a red spot on the body surface 50. As this region projected in red is incised, the affected area 130 becomes gradually exposed, with the result that ICG fluorescence emission intensity becomes stronger, allowing the projection image to turn to orange, yellow, green, and blue. Finally, as shown in FIG. 7B, the affected area 130 is projected as a portion of the region R1*a*, so that if the affected area 130 needs to be excised, it becomes possible to easily recognize and excise a region projected in blue as the affected area 130 requiring excision.

<Hue Range in Third Projection Mode>

Figure 8:
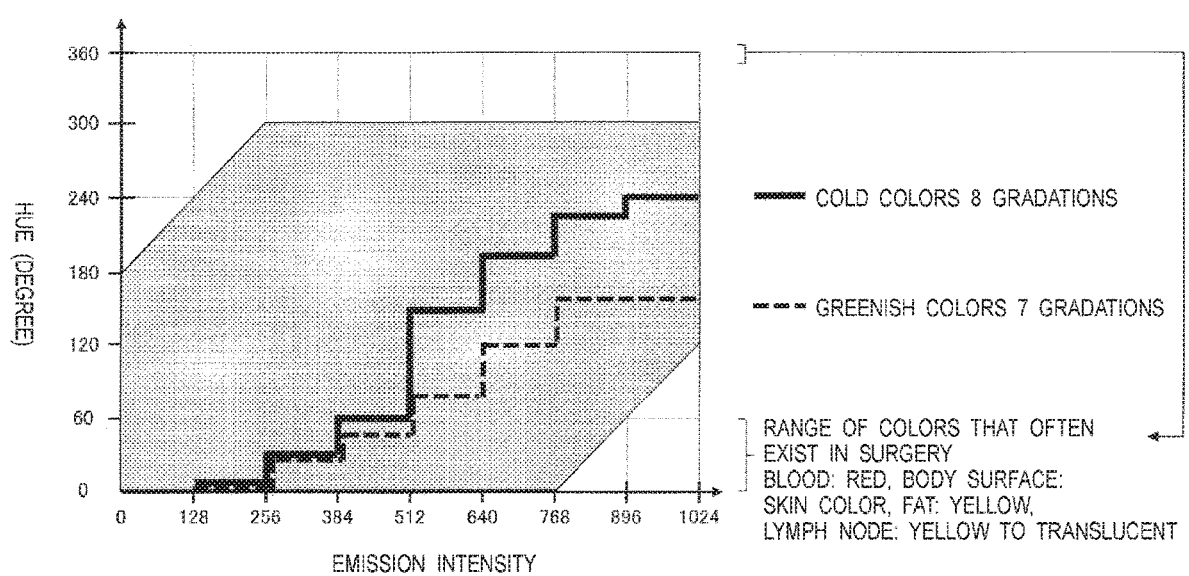
FIG. 8 is a view explaining the range of hue of projection image colors set in the third projection mode.

FIG. 8 is a view explaining the range of hue of projection image colors set in the third projection mode. FIG. 8 shows color allocation for ICG fluorescence emission signal intensity in the case where the projection image is represented in 8 gradations (8-valued) and in the case where the projection image is represented in 7 gradations (7-valued).

In a surgical field, there exist blood, body surface, fat, lymph node, etc. as the background of the projection image. Blood is red, body surface is color of skin (skin color such as pale orange in this embodiment), fat is yellow, and lymph node is yellow to translucent, and hence the background color of the surgical field becomes warm colors. In this embodiment, to facilitate visual distinction of the projection image from its background, a color (i.e. cold color) having a large difference in value and hue from the surgical field background color is used as a color allocated to a region having a relatively strong ICG fluorescence emission intensity. On the other hand, a color (warm color) having a small difference in value and hue from the surgical field background color (human body color) is used as a color allocated to a region having a relatively weak ICG fluorescence emission intensity.

For example, a region having a strong ICG fluorescence emission intensity is represented by a cold color and, according as the intensity becomes weaker, the color is varied to a warmer color. Here, in the case of representing the physical quantity distribution in multicolor like thermography, it is conventionally general to represent a region having a strong intensity by a warm color (red) and to represent a region having a weak intensity by a cold color (blue). In the case of a medical system like this embodiment, however, blood is "red", fat is "yellow", and lymph node is "yellow to translucent", and therefore if a region having a strong intensity is represented by a warm color(red) there is a problem that it is difficult to visually distinguish the projection image from blood, fat, lymph node, etc. Thus, in this embodiment, the region having a strong ICG fluorescence emission intensity is represented by a cold color whereas the region having a weak intensity is represented by a warm color.

For this end, the hue of a color allocated to a region (pixels) having a strongest ICG fluorescence emission intensity is set to a value within the range apart ±60 degrees or more from the range (0 degree or more and 60 degrees or less) of the hue of the surgical field background color. More specifically, the color allocated to a region (pixels) having a strongest ICG fluorescence emission intensity (signal intensity=1024) is set to a color whose hue has a value within the range of 120 degrees or more and 300 degrees or less. This allows the operator (doctor, etc.) to easily visually distinguish the projection image from the background such as blood and body surface.

For example, if the projection color in the case of a high ICG fluorescence intensity is a warm color such as red and orange, the color becomes a color similar to the surroundings of the affected area 130, rendering visual recognition of the excision region difficult. In particular, if the surgery region is a minute region inside an organ, even though the minute region to be excised has been found, the visual recognition of the excision region may become impossible due to unexpected bleeding, etc. On the contrary, if the projection color in the case of a high ICG fluorescence emission intensity is a cold color like blue, even though unexpected bleeding has occurred when excising the minute region, color distinction from blood is clear and hence the visual recognition of the excision region is not hindered, making a precise excision possible.

Alternatively, depending on the hue of an organ where the affected area 130 exists, for example, if the color of the organ is a cold color, setting may be made such that the color changes stepwise from a warm color toward a cold color according as the emission intensity decreases from the highest value. By setting in this manner, the visibility of the affected area 130 projected in a warm color can be enhanced in a cold color of the organ.

With regard to color allocated to a region (pixels) having a signal intensity of 0 or more and 128 or less, the saturation is set to 0% and the value is set to 100%. In other words, the color is set to the same color as the background, i.e. to white. This enables the influence of noise of a weak emission intensity to be eliminated. Moreover, a lighting function by the projection image can be implemented, 3.2 Display Image Generation Process A display image generation process (Step 12 of FIG. 3) will be described. For each of pixels of an infrared image, the CPU 310 sets the hue to any value and sets the saturation to 0%. Furthermore, the CPU 310 sets the value of each pixel of the infrared image depending on the ICG fluorescence emission intensity of each pixel. Here, the value is varied in 1024 gradations depending on the emission intensity. As a result, a display image of full gradation (1024 gradations) having brightness that depends on the fluorescence emission intensity of the affected area 130 is generated and is displayed on the display 160.

3.3 Projection Image Generation Process

Figure 9:
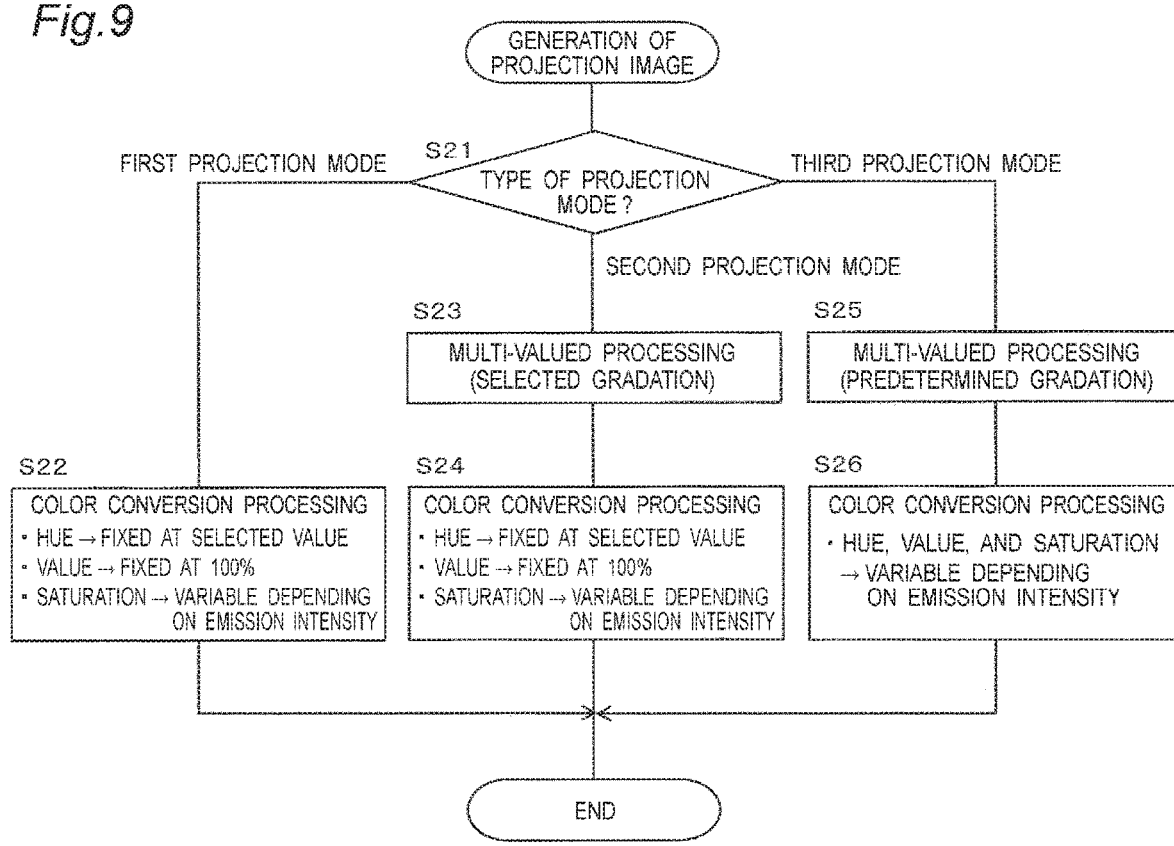
FIG. 9 is a flowchart showing the color conversion processing in the projection modes.

Details (Step 13 of FIG. 13) of a projection image generation process will be described. FIG. 9 is a flowchart showing the projection image generation process.

In FIG. 9, the CPU 310 first determines the type of the projection mode being currently set (Step 21).

If the currently set mode is the first projection mode, the CPU 310 performs color conversion processing in accordance with the first projection mode (Step 22). Specifically, for each pixel of an infrared image, the CPU 310 sets the hue to a value selected by the operator and sets the value to 100% (V100). For example, in the example of FIG. 4, the hue is fixed at H240. Furthermore, the CPU 310 sets the saturation of each pixel of the infrared image, depending on the ICG fluorescence emission intensity of each pixel. Here, the saturation is varied in 1024 gradations depending on the emission intensity. Consequently, a full-gradation projection image is generated.

If the currently set mode is the second projection mode, the CPU 310 performs multi-valued processing in accordance with the second projection mode (Step 23). That is, the original infrared image is subjected to multi-valued processing in gradations such as 2 gradations, 4 gradations, and 8 gradations, set by the operator 140.

For example, in the case of being multi-valued in 2 gradations when the gradation of the original infrared image is 1024 gradations, a threshold in the multi-valued processing is set to 511. And, in the multi-valued processing, as to pixels having gradations of 0 to 511 in the infrared image, their pixel values are converted to 0. On the contrary, as to pixels having gradations of 512 to 1023 in the infrared image, their pixel values are converted to 1023. By such multi-valued processing, 2-gradation image is generated from the infrared image.

In the case of being multi-valued in 4 gradations, three thresholds of 255, 511, and 767 are set. And, as to pixels having gradations of 0 to 255 in the infrared image, their pixel values are converted to 0. As to pixels having gradations of 256 to 511 in the infrared image, their pixel values are converted to 341. For pixels having gradations of 512 to 767 in the infrared image, their pixel values are converted to 682. For pixels having gradations of 768 to 1023 in the infrared image, their pixel values are converted to 1023. By such multi-valued processing, 4-gradation image is generated from the infrared image.

After the multi-valued processing (Step 23), the CPU 310 performs color conversion processing in accordance with the second projection mode (Step 24). Specifically, for each pixel of the multi-valued image, the CPU 310 fixes the hue at a value selected by the operator, varies the saturation, and fixes the value to 100%. For instance, in the example of FIG. 4, the hue is fixed at H240. Furthermore, the CPU 310 sets the saturation of each pixel, depending on the pixel value of each pixel (i.e. the ICG fluorescence emission intensity of each pixel) of the multi-valued image. For example, as shown in FIG. 4, in the case of being set to 2 gradations, the saturation of a pixel having a pixel value of 0 is set to S0, while the saturation of a pixel having a pixel value of 1023 is set to S100. In the case of being set to 4 gradations, the saturation is set to any one of S0, S33, S67, and S100 depending on the pixel value of each pixel of the multi-valued image. In the case of being set to 8 gradations, the saturation of each pixel is set to any one of S0, S14, S29, 543, S57, S71, S86, and S100 depending on the pixel value.

If the currently set mode is the third projection mode, the infrared image is multi-valued in predetermined gradations (e.g. 6, 7, or 8 gradations) set in advance for the third projection mode (Step 25). For instance, in the example shown in FIG. 4, it is multi-valued in 6 gradations.

Afterward, the CPU 310 performs color conversion processing in accordance with the third projection mode (Step 26). Specifically, for each pixel of the multi-valued image, the CPU 310 sets the hue, value, and saturation depending on the pixel value of each pixel. For instance, in the example shown in FIG. 4, the hue is varied in the order of –, H0, H30, H60, H120, and H240 according as the pixel value (ICG fluorescence emission intensity) increases. At that time, the saturation and the value are also varied similarly stepwise. That is, when viewed from the operator, variation occurs in the order of white, red, orange, yellow, green, and blue. Thus, the concentration distribution of ICC accumulated in the affected area 130 in the surgical field is displayed in color, enabling the doctor, etc. performing surgery to easily recognize the concentration distribution of ICG accumulated in the affected area 130.

3.4 Black-and-White Inversion Function

The surgery support system 100 further has a function of inverting black and white in the display mode and the projection modes. That is, when a black-and-white inversion instruction is issued via the operating part 170 by the operator 140, black and white are inverted in the display image and the projection image.

FIG. 10 is a view explaining color conversion processing (black-and-white inverted version) in the case where black and white are inverted in the color conversion processing shown in FIG. 4. For instance, in the display mode, the example of FIG. 4 varied the color from black to white, in other words, increased the value, according as the fluorescence emission intensity increases. On the contrary, the example of FIG. 10 varies the color from white to black, that is, decreases the value, according as the fluorescence emission intensity increases. In the first projection mode, the example of FIG. 4 varied the saturation so that variation from "white" to "blue" occurs according as the emission intensity increases, with the value being fixed at 100%. On the contrary, the example of FIG. 10 varies the value so that variation from "black" to "blue" occurs according as the emission intensity increases, with the saturation being fixed at 100%.

In accordance with a black-and-white inversion instruction from the operator, the CPU 310 switches the color conversion processing to be executed between the color conversion processing shown in FIG. 4 and the color conversion processing shown in FIG. 10, thereby enabling black-and-white inversion in the display mode and the projection modes.

4. Effects, Etc.

As described above, the surgery support system 100 of this embodiment comprises the infrared camera 210 that detects a first region emitting non-visible light, the projector 220 that projects a visible-light image onto a second region (e.g. region R2) including the first region (e.g. regions R1a and R1b) detected by the infrared camera 210, and the control device 30 (or the CPU 310) that generates the visible-light image. The control device 300 varies in a stepwise manner the hues of pixels of the visible-light image, depending on the non-visible light emission intensities at positions corresponding to that pixels within the first region. At that time, the control device 300 sets the hue so that the colors of the pixels of the visible-light image vary stepwise from cold colors to warm colors according as the emission intensities become lower from the highest value.

This configuration allows a visible-light image to be projected in multicolor onto the first region where fluorescence emission has been detected, depending on the ICG fluorescence emission intensity distribution. In particular, use of cold colors in a strong emission intensity region facilitates distinction from warm-colored background seen in the surgical field, improving the visibility of the projected image.

The control device 300 may set the hue of color of pixels corresponding to a highest emission intensity region, to within a range of 120 degrees or more and 300 degrees or less in HSV color space. For example, color of the visible-light image pixels corresponding to the highest emission intensity region may be set to blue or green. The background color in the surgical field is a warm color and its hue range is 0 degree to 60 degrees. Thus, by setting as the above the hue of pixel color corresponding to the highest emission intensity region, it is separated apart 60 degrees or more from the hue of the background color, resulting in an improved visibility of the projected image.

The control device 300 may set stepwise at least one of the saturation and the value of visible-light image pixels, depending on the non-visible-light emission intensities at positions corresponding to that pixels within the first region (see Third Projection Mode of FIG. 4). By making the saturation and the value together with the hue variable depending on the emission intensities, the projected image visibility can further be improved.

The control device 300 may set the settable lowest step color to white. This enables the influence of noise of a weak emission intensity to be eliminated due to the same color as the background color. Moreover, the lighting function by the projection image can be implemented.

The surgery support system 100 may further include the operating part 170 for the operator 140 performing various settings. The control device 300 may include, as the action modes of the projector 220, a plurality of projection modes switchable in accordance with an operation on the operating part 170. The plurality of projection modes include at yeast one of the first projection mode and the second projection mode, and the third projection mode. The first projection mode is a mode in which the saturations of a visible-light image pixels are continuously varied depending on the non-visible-light emission intensities at positions corresponding to that pixels within the first region. The second projection mode is a mode in which the saturations of visible-light image pixels are stepwise varied depending on the non-visible-light emission intensities at positions corresponding to that pixels within the first region. The third projection mode is a mode in which the hues of visible-light image pixels are varied depending on the non-visible-light emission intensities at positions corresponding to that pixels within the first region. By providing a plurality of switchable projection modes, a projection image suitable for the contents or the situation of surgery can be selected.

Other Embodiments

As above, a first embodiment has been described as an exemplification of technique disclosed in the present application. However, the technique of the present disclosure is not limited thereto and is applicable to any embodiments in which changes, permutations, additions, omissions, etc. have properly been made. It is also possible to combine the constituent elements described in the above first embodiment, to provide a new embodiment. Thus, other embodiments will hereinbelow be exemplified.

In the first embodiment, the operator 140 performed various settings for the surgery support system 100 by using and operating the operating part 170 while seeing the display on the display 160. The present disclosure is not limited thereto. Information required for setting may be announced from a speaker connected to the control device 300. And, after hearing that announcement, the operator 140 may speak desired setting into a microphone, to thereby perform a setting operation. Naturally, while seeing buttons on a menu appearing on the display 160, the operator 140 may speak desired setting into the microphone, to thereby perform a selecting operation.

The number of gradations shown in the first embodiment is an example and is properly set depending on the type of the affected area, the case, etc.

Although in the first embodiment the device supporting surgery has been described by way of example, the image projection system of the present disclosure is not limited thereto. For example, also in the case where work needs to be done for objects whose change in state cannot be visually confirmed in e.g. a construction site, a mining site, a building site, or a factory that processes materials, the idea of the image projection system of the present disclosure is applicable. In this case, the intensity distribution colors may be set according to the situation at the above site.

In place of the infrared fluorescent light from ICG of the first embodiment, a fluorescent material may be applied to, kneaded in, or poured into the objects whose change in state cannot be visually confirmed in e.g. a construction site, a mining site, a building site, or a factory that processes materials, to obtain a target to be imaged by the infrared camera 210, onto which a visible-light image is projected. Instead of light emission, a heating portion may be detected by a heat sensor so that a visible-light image is projected onto the heating portion. In this case, a far-infrared ray issued from the heating portion is an example of non-visible light in the present disclosure.

As above, the embodiments have been described as exemplifications of the technique in the present disclosure. To that end, the accompanying drawings and detailed description have been provided.

Accordingly, the constituent elements described in the accompanying drawings and detailed description may encompass not only essential components for solving the problems but also non-essential components for solving the problems, for the exemplifying purposes only. Therefore, immediately from the fact that those non-essential components are described in the accompanying drawings and detailed description, those non-essential components should not be construed as essential.

Since the above embodiments are for the purpose of exemplifying the technique in the present disclosure, various changes, permutations, additions, omissions, etc. can be made without departing from patent claims or their equivalent scope.

The image projection system in the present disclosure is not limited to surgical applications but is applicable to situations where work is done for objects whose change in state cannot be visually confirmed in e.g. a construction site, a mining site, a building site, or a factory that processes materials.

What is claimed is:

1. An image projection apparatus comprising:
   a detector that detects a first region emitting non-visible light;

a projector that projects a visible-light image onto a second region including the first region detected by the detector;

an operating part for an operator performing various settings; and a controller configured to generate the visible-light image so as to vary colors of pixels of the visible-light image in a stepwise manner depending on emission intensities of the non-visible light at positions corresponding to the pixels within the first region, wherein:

the controller is configured to control the projector according to an action mode including a plurality of projection modes switchable in accordance with an operation on the operating part, the plurality of projection modes includes at least one of a first projection mode and a second projection mode, and a third projection mode, the first projection mode is a mode in which saturations of the pixels of the visible-light image are varied continuously depending on the emission intensities of the non-visible light at the positions corresponding to the pixels within the first region, the second projection mode is a mode in which saturations of the pixels of the visible-light image are varied in a stepwise manner depending on the emission intensities of the non-visible light at the positions corresponding to the pixels within the first region, and the third projection mode is a mode in which hues of the pixels of the visible-light image are varied depending on the emission intensities of the non-visible light at the positions corresponding to the pixel within the first region.

2. The image projection apparatus according to claim 1, wherein the controller sets the colors of the pixels of the visible-light image so as to vary the colors in the stepwise manner from cold colors to warm colors according as the emission intensities become lower from a highest value.

3. The image projection apparatus according to claim 2, wherein the controller sets the colors of the pixels of the visible-light image corresponding to a region having the highest emission intensity to blue or green.

4. The image projection apparatus according to claim 1, wherein the controller sets the colors of the pixels corresponding to a region having the highest emission intensity to within a range from 120 degrees to 300 degrees in hue in HSV color space.

5. The image projection apparatus according to claim 1, wherein the controller sets at least one of saturation and value of the pixels of the visible-light image in HSV color space in the stepwise manner depending on the emission intensity of the non-visible light at the positions corresponding to the pixels within the first region.

6. The image projection apparatus according to claim 1, wherein the controller sets the color at a settable lowest step to white.

* * * * *